United States Patent
Maase

[19]

[11] Patent Number: 5,825,474
[45] Date of Patent: Oct. 20, 1998

[54] HEATED OPTICAL PLATEN COVER FOR A FINGERPRINT IMAGING SYSTEM

[75] Inventor: Daniel Frederick Maase, Campbell, Calif.

[73] Assignee: Identix Corporation, Sunnyvale, Calif.

[21] Appl. No.: 549,152

[22] Filed: Oct. 27, 1995

[51] Int. Cl.$^6$ ............................................. G06K 9/00
[52] U.S. Cl. ........................................ 356/71; 382/127
[58] Field of Search ................... 356/71; 382/127

[56] References Cited

U.S. PATENT DOCUMENTS

| | | | |
|---|---|---|---|
| 4,905,293 | 2/1990 | Asai et al. | 356/71 |
| 4,933,976 | 6/1990 | Fishbine et al. | 382/127 |
| 5,416,573 | 5/1995 | Sartor | 356/71 |

FOREIGN PATENT DOCUMENTS

| | | | |
|---|---|---|---|
| 61-28174 | 2/1986 | Japan | 382/127 |
| 4-88586 | 3/1992 | Japan | 382/127 |

*Primary Examiner*—Richard A. Rosenberger
*Attorney, Agent, or Firm*—Fish & Richardson

[57] ABSTRACT

The invention provides a movable cover for a finger receiving surface of an optical platen in a fingerprint imaging device. A heater incorporated into the platen cover applies controlled heat to the finger receiving surface when the cover is closed over the platen. Maintaining the finger receiving surface within a selected temperature range that is at about skin temperature helps to inhibit condensation of moisture from a subject's fingers onto the finger receiving surface.

23 Claims, 3 Drawing Sheets

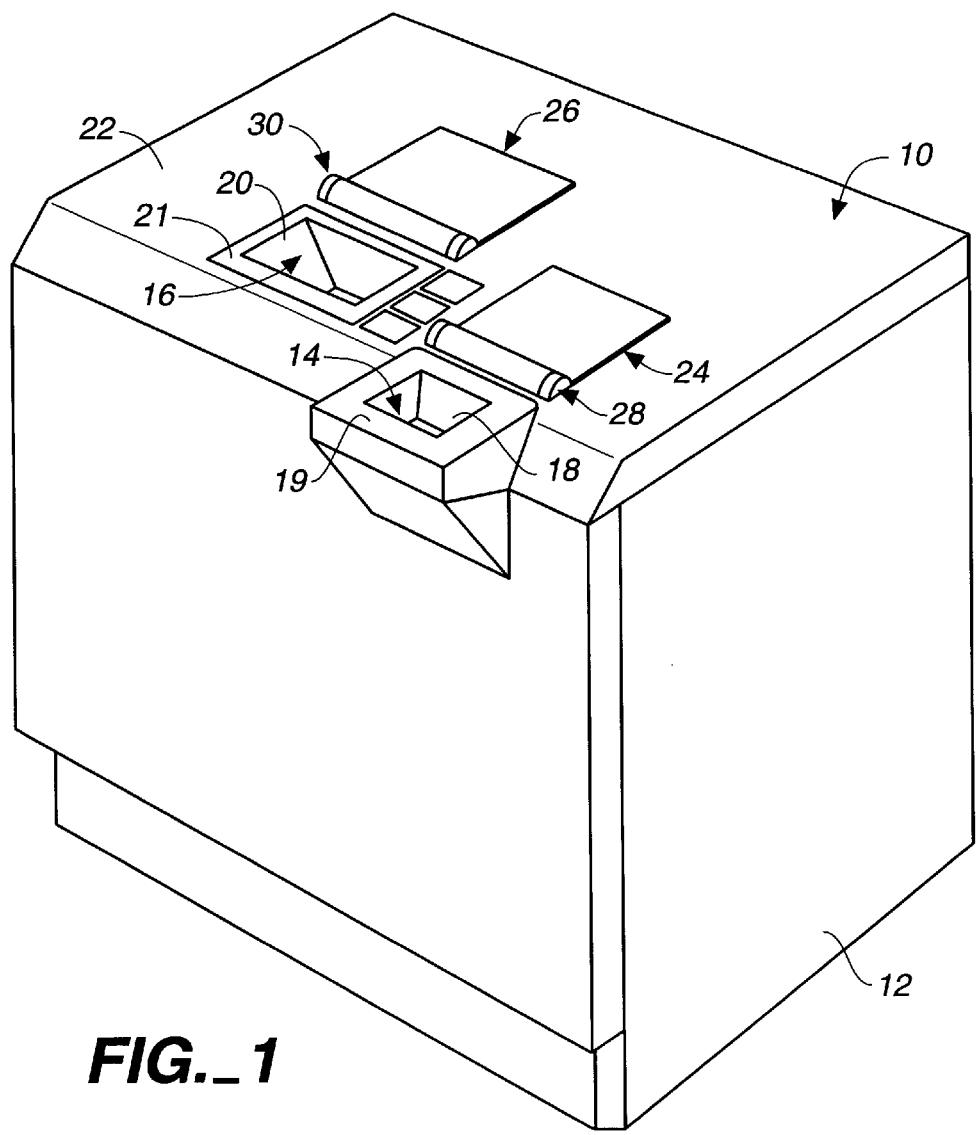
FIG._1
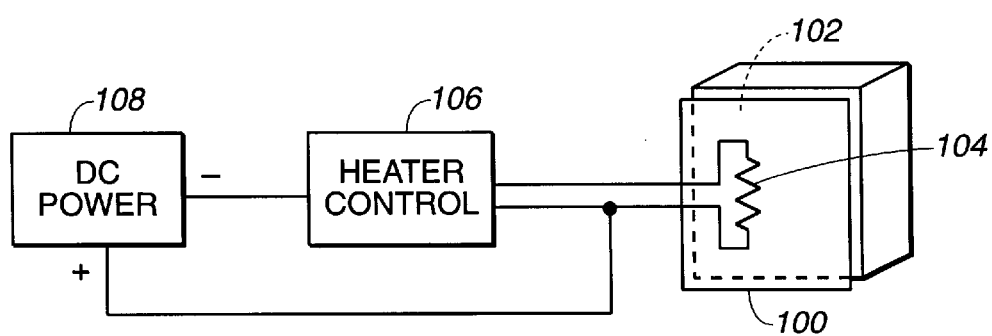
FIG._2

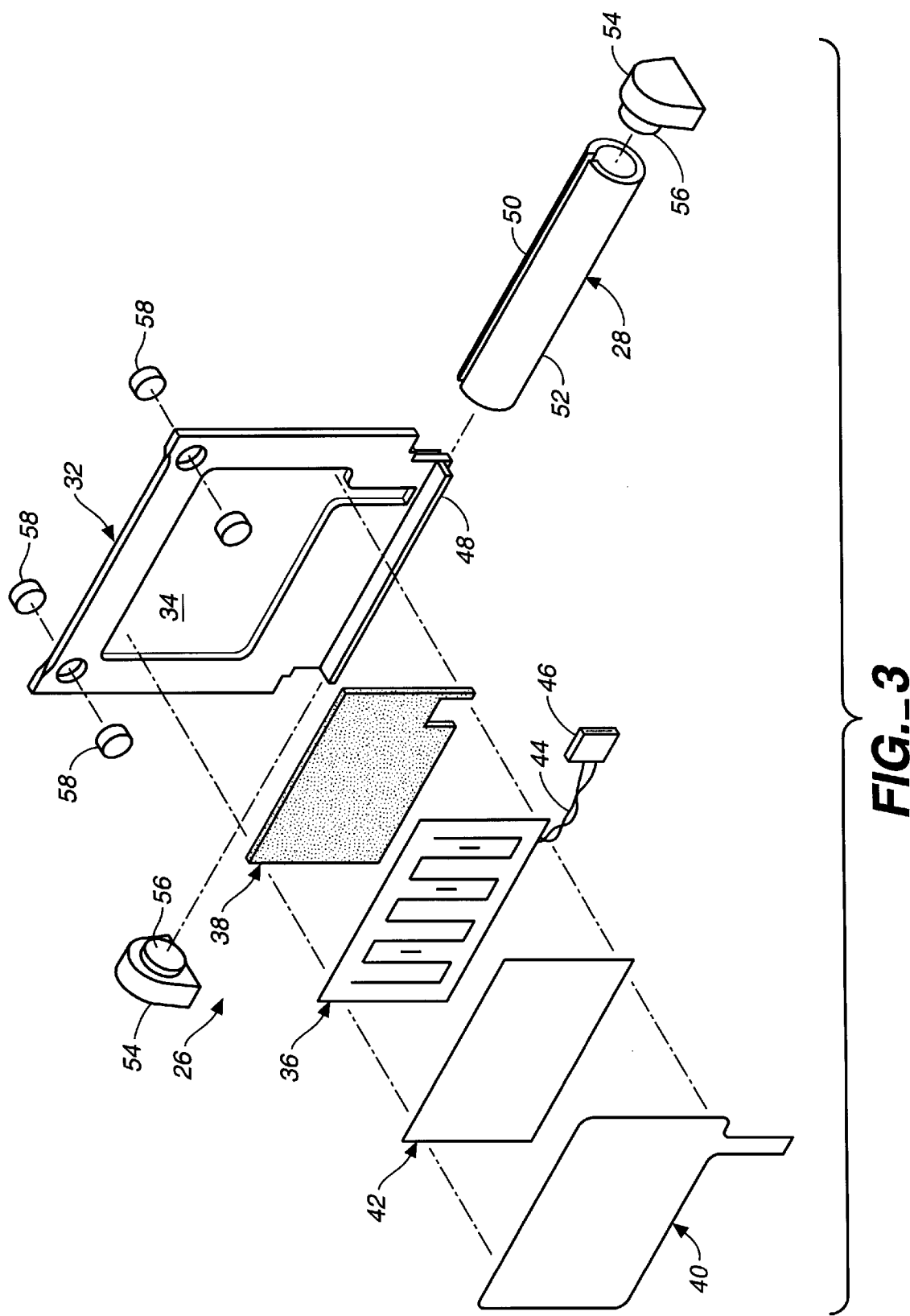
FIG._3

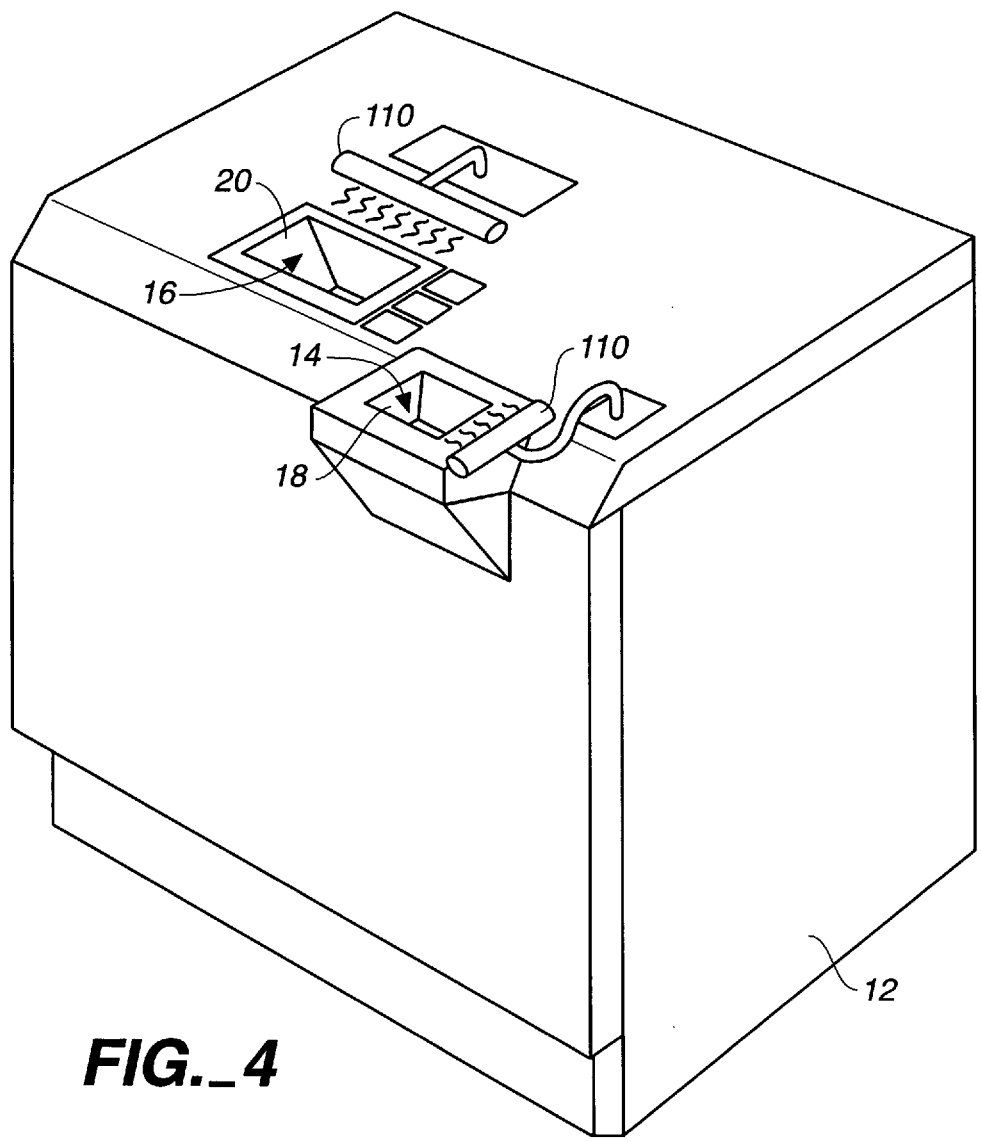
FIG._4

HEATED OPTICAL PLATEN COVER FOR A FINGERPRINT IMAGING SYSTEM

BACKGROUND OF THE INVENTION

1. Field of the Invention

The invention relates to fingerprint imaging devices, and, in particular, to a fingerprint imaging device with a movable cover for the finger receiving surface of an optical platen, and a system for applying heat to the finger receiving surface to inhibit moisture condensation on the finger receiving surface.

2. Description of Prior Art

Electronic fingerprint imaging systems are used to capture fingerprint images that can be used to identify persons for security and law enforcement purposes. An electronically captured image can be reproduced, stored or retrieved efficiently and easily. Persons at one location can quickly transmit an electronic signal representative of the fingerprint image from a computer at one location to a computer at a distant location via a modem connection. Obtaining an electronic image is quick and clean. No ink needs to be applied or removed from a subject's fingers, as with prior art paper and ink systems.

The optical system in an electronic fingerprint capture device typically includes one or more imaging cameras mounted in a frame or enclosure configured to exclude stray light from entering the apertures of the cameras. A prism-shaped optical platen is mounted in the enclosure such that a finger receiving surface of the platen is exposed at a top surface of the enclosure. A light source in the enclosure directs light through the platen to the finger receiving surface at a predetermined angle.

When a subject places a finger on the finger receiving surface, light illuminating covered portions of the finger receiving surface, such as are in contact with the ridges or other raised structures in the surface of the finger, is transmitted at the platen/skin interface and dispersed. Light illuminating bare portions of the finger receiving surface, such as are located below valleys located between the ridge structures of a finger surface or areas around the periphery of the finger, is internally reflected at the platen/air interface. A negative image of a subject's fingerprint is thereby formed and transmitted through the platen and then directed by other optical components to the apertures of the camera or cameras. Raised structures of the finger surface are imaged as dark regions; area not contacting the finger receiving surface are imaged as light regions. This is similar to a traditional ink and paper contact fingerprint.

Dirt, dust and other debris can collect on the finger receiving surface when it is not in use. The finger receiving surface can also be accidentally scratched or otherwise accidentally damaged. The presence of dirt and surface defects in the platen can produce artifacts in the electronic images produced by the image capture device.

Moisture from a subject's fingers can also lead to image problems. Many people naturally have active sweat glands, causing their fingers to always be damp. Other people, in a stressful situation such as being fingerprinted in a police station, will sweat more than they would otherwise. Even a relatively "dry" hand produces a moist vapor. A subject's fingers are approximately 98 degrees fahrenheit, and the finger receiving surface of the optical platen will be room temperature, or about 65–75 degrees fahrenheit. The warm moisture from a subject's warm fingers can condense on the cooler platen.

Moisture that condenses from a subject's fingers onto the finger receiving surface of the optical platen also can significantly degrade the quality of a fingerprint image. Water has an index of refraction $N_W=1.33$, whereas air has an index of refraction $N_A=1.0$. Light illuminating the platen/water interface will be internally reflected when it is incident at an angle $\phi_I$ that is greater or equal to the critical angle $\phi_{W/P}=$ arcsine $(N_W/N_P)$. $\phi_{W/P}$ is significantly greater than the critical angle $\phi_{A/P}$ for the platen/air interface.

The light illuminating the finger receiving surface will generally not be directed at an angle sufficiently great such as to be internally reflected at the platen/water interface. Therefore, areas of the fingerprint receiving surface that are covered by condensed moisture, such as in the valleys between the ridges, and at the periphery of where the subject's finger is pressed to the platen, will be seen by the camera or cameras as dark regions. The imaging camera will see an excessively dark image, with poor definition of fingerprint structures and a shadowy halo around the fingerprint due to the condensed moisture.

There are different approaches to solving the condensed moisture problem. First, the subject can first wipe his hands to remove excess moisture, and even rinse his hands in alcohol to dry them. A second approach is to provide a high pressure blower that directs a flow of air across the finger receiving surface to dry the surface and the subject's fingers. A third approach is to warm the entire optical platen with a heater strip attached to the bottom surface of the platen.

An object of the invention to provide a movable cover for a finger receiving surface of an optical platen in a fingerprint imaging device.

Another object of the invention to provide a system for inhibiting the formation of moisture condensation on a finger receiving surface of an optical platen in a fingerprint imaging device.

SUMMARY OF THE INVENTION

In its broadest sense, the invention provides a movable cover for an optical platen in a fingerprint imaging device, wherein the cover protects the surface of the platen when the imaging device is not in use.

The cover is preferably used in combination with a heating apparatus with a heating element in the cover for maintaining the finger receiving surface of the platen at a predetermined temperature selected to inhibit the formation of moisture condensates on the finger receiving surface.

According to another aspect of the invention, a fingerprint imaging device includes a sealed enclosure containing an optical system for imaging a fingerprint, the optical system including an optical platen having an exposed finger receiving surface. A heater system is structured and arranged to inhibit moisture condensation on the finger receiving surface by applying radiant heat to the finger receiving surface.

More particularly, the invention provides an apparatus for imaging a finger that includes an optical platen having a finger receiving surface, and an enclosure supporting the optical platen and containing an opto-electronic system for providing a signal indicative of surface characteristics of a finger placed on the finger receiving surface. The enclosure is preferably sealed to shield the optical components from ambient light and dust. A platen cover assembly is coupled to the enclosure and has a cover that is movable between an open position covering the finger receiving surface and a closed position exposing the finger receiving surface. Preferably, the platen cover assembly includes a heater system for heating the platen cover such that the finger receiving surface is maintained within a selected temperature range when the platen cover is in the closed position.

The heating system may include a resistive heating element coupled to the platen cover and a heater control for providing electric power to the heating element. The heater control preferably includes a feedback system, including a sensor for providing a first signal indicative of the temperature of the platen cover, and a circuit for adjusting the electric power in response to the first signal.

In a preferred embodiment, the selected temperature range is from approximately 90 degrees to approximately 110 degrees Fahrenheit.

The invention also reduces halo effects due to moisture from a subject's fingers in a fingerprint imaging system, wherein the imaging system includes an optical platen having a finger receiving surface, and a sealed enclosure supporting the optical platen and containing an optoelectronic system for providing a signal indicative of surface characteristics of a finger placed on the finger receiving surface. The halo reducing apparatus includes a platen cover hinged to the enclosure and movable between a closed position covering the finger receiving surface and an open position exposing the finger receiving surface. A heater system heats the platen cover to maintain the finger receiving surface within a selected temperature range when the platen cover is closed.

The invention also provides a method for reducing halo effects due to moisture in a fingerprint imaging system, wherein the imaging system includes an optical platen having a finger receiving surface, and a sealed enclosure supporting the optical platen and containing an optoelectronic system for providing a signal indicative of surface characteristics of a finger placed on the finger receiving surface. The method includes the steps of providing a platen cover hinged to the enclosure and movable between a closed position covering the finger receiving surface and an open position exposing the finger receiving surface, and heating the platen cover to maintain the finger receiving surface within a selected temperature range when the platen cover is closed.

The invention also provides a method of producing an image signal indicative of surface characteristics of a finger, including the steps of first providing an image capture device that includes an enclosure, an optical system contained in the enclosure for producing an optical image of the surface characteristics, and a camera in the enclosure aligned to receive the optical image, wherein the optical system includes an optical platen having an finger receiving surface positioned outside the enclosure. The method also includes the step of providing a platen cover coupled to the enclosure and movable between a closed position covering the finger receiving surface and an open position exposing the finger receiving surface. Then, performing the steps of heating the platen cover while the platen cover is in the closed position such that the finger receiving surface is warmed to approximately a selected temperature above ambient temperature, moving the platen cover to expose the finger receiving surface, positioning the finger on the finger receiving surface while the finger receiving surface is above ambient temperature, producing the optical image of the surface characteristics of the finger with the optical system, and receiving the optical image with the camera and providing the image signal in response.

The method can further include the steps of removing the finger from the finger receiving surface after producing the image signal, moving the platen cover to the closed position, and heating the platen cover again.

BRIEF DESCRIPTION OF THE DRAWINGS

FIG. 1 is a perspective view of an electronic fingerprint capture device according to the invention.

FIG. 2 is a schematic block diagram of a platen heater cover according to the invention.

FIG. 3 is an isometric view of a platen cover assembly.

FIG. 4 is a perspective view of an electronic fingerprint capture device according to another embodiment of the invention.

DESCRIPTION OF THE PREFERRED EMBODIMENTS

Referring to FIG. 1, an electronic fingerprint image scanning device 10 is self-contained within a sealed enclosure 12. A pair of optical platens 14, 16 each are positioned such that their top, finger-receiving surfaces 18 and 20, respectively, are approximately flush with the top surface 22 of the enclosure 12. The finger receiving surfaces 18, 20 are preferably surrounded by bezels 19, 21, respectively.

The platen 14 that has an approximately square-shaped top surface 18 is used to obtain a rolled fingerprint image. The platen 16 having a rectangular-shaped top surface 20 is used to obtain a plain image of the four fingers on a subject's hand.

The platens 14, 16 are fabricated of an optically transparent material, such as, for example, acrylic plastic, polycarbonate plastic, crown glass, flint glass or any other suitable optical material. The finger receiving surfaces 18, 20 can be coated with a transparent, protective elastomeric coating, such as, for example, an acrylic elastomer, a silicone elastomer, an epoxy elastomer, or a urethane elastomer.

The enclosure 12 contains two sets of imaging optics (not shown) for scanning the respective finger-receiving surfaces 18, 20, and processing electronics (not shown) for processing the images and providing a signal representative of a fingerprint image to peripheral devices (not shown).

A roll platen cover 24 is associated with the roll platen 14, and a plain platen cover 26 is associated with the plain platen 16. The covers 24, 26 are each movable on respective hinge assemblies 28, 30 between an open position, depicted in FIG. 1, that exposes the respective finger receiving surfaces 18, 20 and a closed position (not shown) that covers the finger receiving surfaces 18, 20.

Referring now to FIG. 2, each platen cover, generally depicted by reference number 100, has a heater system for heating the platen cover 100 such that the finger receiving surface 102 associated with the platen cover is maintained within a selected temperature range when the platen cover is closed. The heater system preferably includes a resistive heating element 104 incorporated into the platen cover 100, and a heater control 106 electrically coupled to heating element 104 and controlling the power applied through the heating element 104 from a power supply 108.

FIG. 3 shows the plain platen cover assembly 26 in greater detail. The assembly of roll platen cover 24 has similarly arranged parts. Plain platen cover 26 includes a frame 32 having a central opening 34. Set in the opening 34 is a flat, resistive heater element 36 sandwiched between a foam backing 38 that is double coated with acrylic, and a front heater cover 40. A thin acrylic sheet 42 is positioned between the heater element 36 and the front heater cover 40. A pair of wires 44 couple the heater element 36 to a two pin receptacle 46 for connection to the heater control 106.

A bottom edge 48 of platen cover frame 32 has an L-shaped cross section structured and arranged to fit in a groove 50 defined in a rotatable cylinder hinge 52. A pair of supports 54, each having a round post 56 that fits into a cylindrical opening at an end of the cylinder hinge 52, are fixed to the top surface 22 of enclosure 12. Cover 26 is free to rotate on cylinder hinge 52 between an open position, shown in FIG. 1, exposing the finger receiving surface 20, and a closed position (not shown) covering the finger receiving surface 20.

Resilient bumpers 58 are set in the corners of frame 32 to keep cover 26 from scratching finger receiving surface 16 or top surface 22 of enclosure 12.

Heater element 36 is preferably a high temperature coefficient of resistance (TCR) wire configured in a planar arrangement, and that is electrically insulated, preferably with a polymeric coating, such as Kapton®. Suitable heating elements can be obtained from Minco Products, Inc. located in Minneapolis, Minn. Heater controller 106 provides electrical power to heater element 36. It is preferred that a sensorless DC temperature controller be used for heater controller 106, for example, controller model CT198, which is also available from Minco Products, Inc. This type of controller uses the temperature dependent resistance of the high TCR heater element to sense and control heat output. The heater element 36 is periodically powered momentarily to check the element temperature. When the element temperature is above a set point, power is turned off. If the element temperature is below the set point, the power is turned on until the temperature reaches the set point. The controller then returns to the periodic scanning mode.

While the above-described embodiment incorporates the platen heater element into the platen cover, the cover and heater element can be separate items and different types of heat sources can be used. Referring now to FIG. 4, the heating system may include, for example, a radiant heat source 110, such as, e.g. an incandescent lamp or an IR lamp, positioned on the top of enclosure 12 and directing radiant heat to the finger receiving surface.

Also, heater controller 106 can be configured to use a separate temperature sensor (not shown), such as, for example, a thermostat or thermocouple embedded in the heater or the platen, to monitor the temperature of the cover or the finger receiving surface for feedback control.

The platen covers 24, 26 are normally kept closed. The heating system for each maintains the covers 24, 26 and the respective finger receiving surfaces 18, 20 in the selected temperature range above ambient temperature. When an operator desires to obtain a fingerprint image, for example a rolled image, of a subject's finger, she first moves cover 24 to the open position, places the subject's finger on finger receiving surface 18 while the finger receiving surface 18 is still warm, and obtains the image with the imaging device in the normal manner. After obtaining the image, she removes the finger from the finger receiving surface 18 and closes the cover again.

The invention thus provides advantages not found in prior art systems. The platen cover protects the finger receiving surface from dirt, dust and debris, and helps to prevent accidental damage to the finger receiving surface.

The heater system heats the finger receiving surface and thereby inhibits condensation of moisture from a subject's fingers onto the finger receiving surface of the optical platen. The optical platen can be field serviced without having to detach and reattach a heater element directly to the bottom of the platen. The invention replaces noisy blowers and associated ducts for directing air to the finger receiving surface with a much simpler system.

The particular embodiments of the invention discussed above are intended to be illustrative of the invention, and not limiting. Other embodiments are within the following claims.

What is claimed is:

1. An apparatus for imaging a finger, comprising:
    an optical platen having a finger receiving surface;
    an enclosure supporting the optical platen and containing an opto-electronic system for providing a signal indicative of surface characteristics of a finger placed on the finger receiving surface;
    a platen cover coupled to the enclosure and movable between a first position covering the finger receiving surface and a second position exposing the finger receiving surface; and
    means for heating the platen cover such that the finger receiving surface is maintained within a selected temperature range when the platen cover is in the first position.

2. The apparatus of claim 1, wherein the heating means comprises a resistive heating element coupled to the platen cover and a heater control for providing electric power to the heating element.

3. The apparatus of claim 2, wherein the heater control comprises a feedback system, including a sensor for providing a first signal indicative of the temperature of the platen cover, and a circuit for adjusting the electric power in response to the first signal.

4. The apparatus of claim 1, wherein the selected temperature range is from approximately 90 degrees to approximately 110 degrees fahrenheit.

5. An apparatus, comprising:
    an optical platen having a finger receiving surface;
    an enclosure supporting the optical platen and containing an opto-electronic system for providing a signal indicative of surface characteristics of a finger placed on the finger receiving surface;
    a platen cover hinged to the enclosure and movable between a first position covering the finger receiving surface and a second position exposing the finger receiving surface; and
    a system for heating the platen cover such that the finger receiving surface is maintained within a selected temperature range when the platen cover is in the first position.

6. The apparatus of claim 5, wherein the heating system comprises a resistive heating element coupled to the platen cover and a heater control for providing electric power to the heating element.

7. The apparatus of claim 6, wherein the heater control comprises a feedback system, including a sensor for providing a first signal indicative of the temperature of the platen cover, and a circuit for adjusting the electric power in response to the first signal.

8. The apparatus of claim 5, wherein the selected temperature range is from approximately 90 degrees to approximately 110 degrees fahrenheit.

9. An apparatus for reducing halo effects due to moisture in a fingerprint imaging system that includes an optical platen having a finger receiving surface and an enclosure supporting the optical platen and containing an opto-electronic system for providing a signal indicative of surface characteristics of a finger placed on the finger receiving surface, the apparatus comprising:
    a platen cover hinged to the enclosure and movable between a first position covering the finger receiving surface and a second position exposing the finger receiving surface; and a system for heating the platen cover such that the finger receiving surface is maintained within a selected temperature range when the platen cover is in the first position.

10. A method for reducing halo effects due to moisture in a fingerprint imaging system that includes an optical platen having a finger receiving surface and an enclosure supporting the optical platen and containing an opto-electronic system for providing a signal indicative of surface characteristics of a finger placed on the finger receiving surface, the method comprising:

providing a platen cover hinged to the enclosure and movable between a first position covering the finger receiving surface and a second position exposing the finger receiving surface; and heating the platen cover such that the finger receiving surface is maintained within a selected temperature range when the platen cover is in the first position.

11. A fingerprint imaging device, comprising the combination of:

an optical platen having a finger receiving surface;

a sealed enclosure, including an opening in an upward facing surface for placing the optical platen such that the finger receiving surface is exposed, and a cover that is movable from a closed position for covering the finger receiving surface to an open position for exposing the finger receiving surface; and a heating element in the cover structured and arranged to apply heat to the finger receiving surface when the cover is in the closed position.

12. The fingerprint imaging device of claim 11, wherein a heater control is coupled to the heating element for controlling the power applied to the heating element such that the finger receiving surface is maintained within a selected temperature range for inhibiting the formation of moisture condensates upon the finger receiving surface when a finger is applied to the finger receiving surface.

13. The fingerprint imaging device of claim 12, wherein the heater element is a resistive heater element, and wherein the heater control comprises a feedback system, including a sensor for providing a first signal indicative of the temperature of the platen cover, and a circuit for adjusting the electric power in response to the first signal.

14. The apparatus of claim 12, wherein the selected temperature range is from approximately 90 degrees to approximately 110 degrees fahrenheit.

15. A fingerprint imaging device, including:

a sealed enclosure containing an optical system for imaging a fingerprint, the optical system including an optical platen having an exposed finger receiving surface; and an apparatus structured and arranged to inhibit moisture condensation on the finger receiving surface by applying radiant heat to the finger receiving surface.

16. The fingerprint imaging device of claim 15, wherein the moisture inhibiting apparatus comprises:

a platen cover that is movable between a first position covering the finger receiving surface and a second position exposing the finger receiving surface;

a resistive heater element in the platen cover; and a heater controller providing electrical power to the heater element.

17. A method for inhibiting condensation of moisture from a subject's finger on a finger receiving surface of an optical platen in a fingerprint image capture device, comprising the steps of:

applying radiant heat to the finger receiving surface; and controlling the applied radiant heat to maintain the temperature of the finger receiving surface within a selected temperature range.

18. The method of claim 17, wherein the step of applying radiant heat comprises heating a movable platen cover while the platen cover is positioned over the finger receiving surface.

19. The method of claim 18, wherein the step of controlling comprises providing power to a resistive heater element in the platen cover when the heater element temperature is below a set point temperature.

20. A method of producing an image signal indicative of surface characteristics of a finger, comprising the steps of:

providing an image capture device that includes an enclosure, an optical system contained in the enclosure for producing an optical image of the surface characteristics, and a camera in the enclosure aligned to receive the optical image, wherein the optical system includes a optical platen having an finger receiving surface positioned exterior the enclosure;

providing a platen cover coupled to the enclosure and movable between a closed position covering the finger receiving surface and an open position exposing the finger receiving surface;

heating the platen cover while the platen cover is in the closed position such that the finger receiving surface is warmed to approximately a selected temperature above ambient temperature;

moving the platen cover to expose the finger receiving surface;

positioning the finger on the finger receiving surface while the finger receiving surface is above ambient temperature;

producing the optical image of the surface characteristics of the finger with the optical system; and receiving the optical image with the camera and providing the image signal in response.

21. The method of claim 20, wherein the selected temperature is in a range from approximately 90 to approximately 110 degrees Fahrenheit.

22. The method of claim 20, wherein the platen cover is hinged to the enclosure.

23. The method of claim 20, further comprising the steps of removing the finger from the finger receiving surface after producing the image signal, moving the platen cover to the closed position, and heating the platen cover again.

* * * * *

UNITED STATES PATENT AND TRADEMARK OFFICE
CERTIFICATE OF CORRECTION

PATENT NO.       : 5,825,474
DATED            : October 20, 1998
INVENTOR(S)      : Maase It is certified that error appears in the above-identified patent and that said Letters Patent is hereby corrected as shown below:

Claims:

Claim 20, column 8, line 30, delete "an" and substitute therewith --a--.

Signed and Sealed this

Fifteenth Day of June, 1999

*Attest:*

Q. TODD DICKINSON

*Attesting Officer*     *Acting Commissioner of Patents and Trademarks*